US008652846B2

(12) United States Patent
Habib et al.

(10) Patent No.: US 8,652,846 B2
(45) Date of Patent: Feb. 18, 2014

(54) MEDIUM DERIVED FROM STEM CELLS AS A PHARMACEUTICAL COMPOSITION

(75) Inventors: Nagy A. Habib, London (GB); Myrtle Gordon, London (GB)

(73) Assignee: Omnicyte Limited, London (GB)

( * ) Notice: Subject to any disclaimer, the term of this patent is extended or adjusted under 35 U.S.C. 154(b) by 97 days.

(21) Appl. No.: 13/124,111

(22) PCT Filed: Oct. 2, 2009

(86) PCT No.: PCT/GB2009/002350
§ 371 (c)(1),
(2), (4) Date: Jul. 6, 2011

(87) PCT Pub. No.: WO2010/043847
PCT Pub. Date: Apr. 22, 2010

(65) Prior Publication Data
US 2011/0262392 A1    Oct. 27, 2011

(30) Foreign Application Priority Data

Oct. 13, 2008    (GB) .................................. 0818725.4

(51) Int. Cl.
*C12N 5/00*    (2006.01)
*C12N 5/02*    (2006.01)

(52) U.S. Cl.
USPC ........................... 435/384; 435/386; 435/391

(58) Field of Classification Search
None
See application file for complete search history.

(56) References Cited

U.S. PATENT DOCUMENTS

| | | | |
|---|---|---|---|
| 5,807,686 A | | 9/1998 | Wagner et al. |
| 6,930,222 B2 * | | 8/2005 | Yu ..................................... 800/10 |
| 7,202,080 B2 | | 4/2007 | Ramiya et al. |
| 8,021,882 B2 * | | 9/2011 | Johnstone et al. ............. 435/404 |
| 8,172,784 B2 * | | 5/2012 | Yarmush et al. .............. 604/6.09 |
| 8,372,797 B2 * | | 2/2013 | Ichim ................................ 514/1 |
| 2006/0165667 A1 | | 7/2006 | Laughlin et al. |
| 2008/0145442 A1 | | 6/2008 | Yarmush et al. |

FOREIGN PATENT DOCUMENTS

| | | |
|---|---|---|
| CA | 2426987 A1 | 5/2002 |
| WO | WO 99/40180 A2 | 8/1999 |
| WO | WO 01/71016 A1 | 9/2001 |
| WO | WO 01/94420 A1 | 12/2001 |
| WO | WO 02/36751 A2 | 5/2002 |
| WO | WO 02/064748 A2 | 8/2002 |
| WO | WO 02/079457 A1 | 10/2002 |
| WO | WO 03/014326 A2 | 2/2003 |
| WO | WO 03/055989 A2 | 7/2003 |
| WO | WO 03/080822 A1 | 10/2003 |
| WO | WO 03/083070 A2 | 10/2003 |
| WO | WO 2005/059113 A1 | 6/2005 |
| WO | WO 2007/022515 A2 | 2/2007 |
| WO | WO 2008/082525 A1 | 7/2008 |
| WO | WO 2009/105044 A1 | 8/2009 |

OTHER PUBLICATIONS

Anonymous. 2006 "Current clinical applications of stem cells" *Eurostem cell—European Consortium for Stem Cell Research* retrieved from Internet URL:http://archive.eurostemcell.org/Documents/Research/ClinicalWorkshopMarch06-Report.pdf, pp. 1-2.
Fleischmann, G. 2007 "Symposium in stem cell repair and regeneration" *Cloning and Stem Cells* 9:141-143.
Gordon, M. et al. 2006 "Characterization and clinical application of human CD34+ stem/progenitor cell populations mobilized into the blood by granulocyte colony-stimulating factor" *Stem Cells* 24: 1822-1830.
Gordon, M. 2008 "Stem Cells for regenerative medicine—Biological attributes and clinical application" *Experimental Hematology* 36: 726-732.
Guo, Y. et al. 2006 "Murine embryonic cells secrete cytokines/growth modulators that enhance cell survival/anti-apoptosis and stimulate colony formation of murine hematopoietic progenitor cells" *Stem Cells* 24: 850-856.
Majka, M. et al. 2001 "Numerous growth factors, cytokines; and chemokines are secreted by human CD34+ cells, myeloblasts, erythroblasts, and megakaroblasts and regulate normal hematopoiesis in an autocrine/paracrine manner" *Blood* 97: 3075-3085.
Ratajczak, M.Z et al. 2009 "A multi-instrumental approach to identify and purify very small embryonic like stem cells (VSELs) from adult tissues" *Micron* 40: 386-393.
Szlosarek, P. and Balkwill, F.R. 2003 "Tumor necrosis factor alpha: a potential target for the therapy of solid tumors" *The Lancet Oncology* 4: 565-573.
Timmers, L. et al. 2008 "Reduction of myocardial infarct size by human mesenchymal stem cell conditioned medium" *Stem Cell Research* 1: 129-137.
Togel, F. et al. 2007 "Vasculotropic, paracrine actions of infused mesenchymal stem cells are important to the recovery from acute kidney injury" *American Journal of Physiology* 292: F1626-F1635.
Xu, Y.-X. et al. 2009 "Mesenchymal Stem Cells Treated with Rat Pancreatic Extract Secrete Cytokines that Improve the Glycometabolism of Diabetic Rats" *Transplantation Proceedings* 41: 1878-1884.
Bucala, R. et al. (1994) "Circulating fibrocytes define a new leukocyte subpopulation that mediates tissue repair" *Molecular Medicine*, 1:71-81.
Deans, R.J. et al. (2000) "Mesenchymal stem cells: biology and potential clinical uses" Experimental Hematology, 28:875-884.
De Bari, Cosimo et al. (2001) "Multipotent Mesenchymal Stem Cells From Adult Human Synovial Membrane" *Arthritis & Rheumatism* 44: 1928-1942.
Ferrero, D. (1998) "A single step density gradient separation for large scale enrichment of mobilized peripheral blood progenitor cells collected for autotransplantation" *Bone Marrow Transplantation* 21: 409-413.
Gordon et al. 1996 "Phenotype and progeny of primitive adherent hematopoietic progenitors" Leukemia 10:1347-1353.

(Continued)

*Primary Examiner* — Michail Belyavskyi
(74) *Attorney, Agent, or Firm* — Knobbe Martens Olson & Bear, LLP (57) ABSTRACT

The invention provides an apoptosis-modulating cell-free composition comprising conditioned extracellular medium of a stem cell and uses thereof, particularly therapeutic uses. Also provided is a method of obtaining such a composition and an in vitro method of modulating apoptosis.

2 Claims, 5 Drawing Sheets

(56) References Cited

OTHER PUBLICATIONS

Javazon, E.H. et al. (2004) "Mesenchymal stem cells: paradoxes of passaging" Experimental hematology, 32: 414-425.

Jiang, Y. et al. (2002) "Pluripotency of mesenchymal stem cells derived from adult marrow" Nature, 418:41-49.

Kiem, H.-P. et al. 1999 "Improved gene transfer into canine hematopoietic repopulating cells using CD34-enriched marrow cells in combination with a gibbon ape leukemia virus-pseudotype retroviral vector" *Gene Therapy* 6: 966-972.

Romero-Ramos, Marina et al. (2002) "Neuronal Differentiation of Stem Cells Isloated From Adult Muscle" *Journal of Neuroscience Research* 69: 894-907.

Sugiura et al. 1992 "Effect of human immunodeficiency virus-1 envelope glycoprotein on in vitro hematopoiesis of umbilical cord blood" Blood 80:1463-1469.

Verfaillie, C.M. (2002) "Adult stem cells: assessing the case for pluripotency" Trends in Cell Biology, 12:502-508.

Vodyanik, M.A. et al. 2010 "A mesoderm-derived precursor for mesenchymal stem and endothelial cells" *Cell Stem Cell*, vol. 7, Issue 6, 718-729.

Young et al. 2001 "Human reserve pluripotent mesenchymal stem cells are present in the connective tissues of skeletal muscle and dermis derived from fetal, adult, and geriatric donors" The Anatomical Record 264:51-62.

* cited by examiner

MEDIUM DERIVED FROM STEM CELLS AS A PHARMACEUTICAL COMPOSITION

RELATED APPLICATIONS

This application is a U.S. National Phase of International Application No.: PCT/GB2009/002350, filed Oct. 2, 2009, designating the U.S. and published in English on Apr. 22, 2010 as WO 2010/043847 A1, which claims the benefit of United Kingdom Application No. 0818725.4, filed Oct. 13, 2008.

FIELD OF THE INVENTION

The present invention relates to a factor capable of modulating apoptosis, which factor is secreted by a stem cell, in particular by a type of stem cell called OmniCyte, and the use of this factor in therapy such as cancer therapy. A conditioned extracellular medium of a stem cell, preferably an OmniCyte, methods of preparing the conditioned medium and uses thereof are provided.

BACKGROUND

The insufficient delivery of therapeutic molecules to tumour cells is one of the reasons for the failure of treatment strategies for cancer. There is, therefore, a great need for the identification of cellular vectors that specifically approach cancer stem cells to deliver therapeutic molecules. Recent studies have demonstrated the tropism of normal neuronal stem cells and bone marrow (BM) derived stem cells for cancer. Implanted neuronal stem cells surrounded the expanding brain tumour mass and even attached to the distantly infiltrating tumour cells. It has been shown that this homing property could be exploited to deliver various therapeutic agents to tumours.

The tropism of stem cells for cancer is not limited to the stem cells of neuroectodermal origin or central nervous system. Several recent studies have shown that bone marrow (BM) mesenchymal stem cells (MSC) could be used as vehicles for the treatment of brain tumours.

However, MSC might undergo spontaneous transformation following long-term in vitro culture, causing concerns about their tumorigenicity and subsequent use for clinical therapy.

Another BM-derived stem cell population that may have the potential to be used to target cancer stem cells comprises haematopoietic stem cells. Haematopoietic stem cells (HSC) participate in tissue regeneration by promoting immune response and/or differentiating into functional cells involved in the repair of damaged tissue. HSC are $CD34^+$ and $CD133^+$ and have the advantage that they can be prospectively isolated from BM-aspirate or mobilised peripheral blood as a morphologically and immunophenotypically defined cell population. They possess the ability to self-renew and are an unlimited source of potential cellular vectors.

HSC express the chemokine receptor CXCR4. The ligand of this receptor, stromal-derived growth factor-1 (SDF-1), was found to be expressed by solid tumours, which could provide the basis for directing and homing of reparative cells such as HSC to tumours.

The SDF-1 and CXCR4 axis is an important regulator of stem cell trafficking and migration and also regulates cell chemotaxis and adhesion. It has been suggested that HSC have a tropism for cancer. Their trophic effects may have important clinical use, as HSC could be used as vehicles for the delivery of therapeutic agents to the site of the tumours. Moreover, modified HSC can produce high concentrations of anti-tumour agents directly within the tumour mass, impact tumour growth and progression and deliver site-specific cytotoxic agents.

There remains a great need for ways to improve the success of anti-cancer treatments, and treatments of anti-proliferative disorders in general.

DESCRIPTION OF THE INVENTION

The present inventor set out to test if a certain class of stem cells, known in the art as "OmniCytes", could be used as vehicles for delivering drugs to cancer cells. OmniCytes are a class of stem cells which are CD34+ and adherent and which are described in WO 2005/059113, which is incorporated herein by reference. Cancer cell lines were treated with a pro-apoptotic agent such as staurosporine, cisplatin or paclitaxel and cultured with OmniCytes.

Surprisingly, when staurosporine, cisplatin or paclitaxel were used alone, they induced higher levels of apoptosis in the cancer cells than when the cancer cells were also co-cultured with OmniCytes. This would suggest that during co-culture, the OmniCytes protect the cancer cells against the pro-apoptotic effects of agents such as staurosporine, cisplatin or paclitaxel. These findings suggest that OmniCytes may not be a good candidate for cytostatic drug delivery.

Nevertheless, the inventor carried out further tests, which included a similar analysis, except that instead of co-culturing the OmniCytes with the cancer cells, a Transwell assay was used. The Transwell system allows the exchange of soluble factors, but prevents cell-cell contact. To his great surprise, the inventor found that in this assay the OmniCytes potentiated the effect of the pro-apoptotic agent. It would seem that stem cells, in particular OmniCytes, secrete one or more factor(s) which can enhance the pro-apoptotic effect of drugs used to treat hyperproliferative disorders such as cancer. Thus, this secreted factor is capable of modulating apoptosis and so it is referred to herein as an apoptosis-modulating factor.

This finding has led the inventor to propose the use of this apoptosis-modulating factor in therapeutic applications such as the treatment of a hyperproliferative disorder, particularly cancer.

The apoptosis-modulating factor may conveniently be obtained by culturing the stem cells, preferably OmniCytes, in a medium and then collecting the extracellular medium after a suitable length of time such as 12-72 hours, preferably 24-60 hours, most preferably 24-28 hours, e.g. 36 hours. During culture, the stem cells, secrete the apoptosis-modulating factor into the extracellular medium. Thus, the stem cell will be cultured in the medium for a sufficient length of time to allow secretion of the apoptosis-modulating factor to yield an apoptosis-modulating conditioned extracellular medium. Such culture will preferably be carried out for at least 2, 3, 4, 5, 6, 7, 8, 9 or 10 hours, more preferably at least 10, 11, 12, 13, 14, 15, 16, 17, 18, 19 or 20 hours. Medium which has been exposed to stem cells, preferably OmniCytes, for a suitable length of time may be referred to as "conditioned medium" or "conditioned extracellular medium". These terms are used interchangeably herein. Standard culture conditions, which are well known in the art, may be used, for example culture at about 37° C. in 5% $CO_2$/95% air.

The medium in which the stem cell, preferably OmniCyte, is cultured to obtain a conditioned (extracellular) medium may be any culture medium suitable for stem cell culture. The skilled person will be aware of suitable media, but by way of example α-Minimum Essential Medium (α-MEM) (Gibco, UK), methylcellulose medium, Dulbecco's Modified Eagle's Medium (DMEM), StemSpan® Serum-Free Expansion Medium (SFEM), StemSpan® H3000 (both available from STEMCELL Technologies, 570 West Seventh Avenue, Suite 400, Vancouver, BC, Canada V5Z 1B3), Iscove's Modified Dulbecco's Medium (IMDM), McCoy's 5A Medium and RPMI 1640 are named herein, each of which may be supplemented with suitable factors such as serum, e.g. 1-30% foetal bovine serum (FBS) (Biosera, UK) and/or cytokines, for example GM-MIX cytokines (SCF 20 ng/mL, GM-SCF 1 ng/mL, IL-3 5 ng/mL, GSCF 100 ng/mL). Preferably, the medium is $\alpha$-MEM supplemented with 30% FBS and 10% GM-MIX. Thus, the conditioned medium may contain serum, but in some embodiments it is serum-free.

The conditioned extracellular medium may be processed to enrich it for the apoptosis-modulating factor. Enrichment may yield an enriched fraction which contains a higher percentage (w/w) of the apoptosis-modulating factor than the non-enriched conditioned extracellular medium. Preferably, the apoptosis-modulating factor makes up at least 1% (w/w) of the protein contained in the enriched fraction, more preferably at least 5, 10, 15, 20 or 25% (w/w), most preferably at least 30, 40, 50, 60, 70, 80 or 90% (w/w).

The conditioned extracellular medium may also be processed to purify the apoptosis-modulating factor. Purification may be full or partial, so after the purification the factor may be free or substantially free of any other protein.

Enrichment or purification may involve a number of different techniques. Centrifugation may be used, for example to separate proteins from contaminants such as nucleic acid molecules. One or more chromatographic steps may be used to separate proteins on the basis of size (gel filtration chromatography), charge (ion exchange chromatography), or hydrophobicity (hydrophobic interaction chromatography). The various chromatographic methods are well known in the art.

The various fractions obtained using chromatographic methods may be tested for apoptosis-modulating activity using for example Fluorescence activated cell sorting (FACS) or immunohistochemistry as described below. Purity may be assessed using polyacrylamide gel electrophoresis (PAGE), for example SDS-PAGE or non-denaturing PAGE, or by using high performance liquid chromatography. Ultrafiltration may be used to concentrate the protein and/or to remove salts and other small proteinaceous or non-proteinaceous molecules.

It is also envisaged that instead of using an isolated apoptosis-modulating factor which can be obtained from the conditioned medium, the conditioned medium as defined above or a fraction thereof, for example a fraction enriched for the apoptosis modulating factor, may itself be used in the applications disclosed herein.

Thus, there is provided an apoptosis-modulating factor for use in therapy, wherein said factor is secreted by a stem cell, preferably by an OmniCyte. In a preferred embodiment, there is provided an apoptosis-modulating factor for use in potentiating the effect of a pro-apoptotic agent on hyperproliferative cells, in particular cancer cells, wherein said factor is secreted by a stem cell, preferably by an OmniCyte.

Alternatively viewed, there is provided the use of an apoptosis-modulating factor in the manufacture of a medicament for the treatment of a hyperproliferative disorder in a subject, in particular cancer, wherein said factor is secreted by a stem cell, preferably by an OmniCyte. Preferably, the medicament potentiates the effect of a pro-apoptotic agent on hyperproliferative cells present in the subject.

In some embodiments, conditioned medium as defined herein is used, so there is provided an apoptosis-modulating conditioned medium for use in therapy, wherein said conditioned medium is obtainable or obtained by culturing stem cells, preferably OmniCytes and collecting the extracellular medium.

In a preferred embodiment, there is provided an apoptosis-modulating conditioned medium for use in potentiating the effect of a pro-apoptotic agent on hyperproliferative cells, in particular cancer cells, wherein said conditioned medium is obtainable or obtained by culturing a stem cell, preferably an OmniCyte in a medium and collecting the conditioned extracellular medium.

Alternatively viewed, there is provided the use of an apoptosis-modulating conditioned medium in the manufacture of a medicament for the treatment of a hyperproliferative disorder in a subject, in particular cancer, wherein said conditioned medium is obtainable or obtained by culturing a stem cell, preferably an OmniCyte in a medium and collecting the conditioned extracellular medium. Preferably, the medicament potentiates the effect of a pro-apoptotic agent on hyperproliferative cells present in the subject.

The apoptosis-modulating conditioned medium contains the apoptosis-modulating factor, so any reference herein to an apoptosis-modulating factor should be taken to include a reference to an apoptosis-modulating conditioned medium. However, the term "isolated apoptosis-modulating factor" does not encompass conditioned medium. By "isolated" is meant free from any other proteinaceous matter, cellular debris and nucleic acid. The factor may preferably be an isolated agent or a mixture of isolated agents.

When conditioned medium is used, this may prior to administration to the subject be subjected to one or more processing steps, for example sterilisation, filtering, centrifugation, or any other technique known in the art to remove contaminants. Thus, preferably the conditioned medium is sterile and/or free of contaminants selected from heavy metals, salts and/or nucleic acids.

In one aspect, there is provided an apoptosis-modulating cell-free composition comprising or consisting of the conditioned extracellular medium of a stem cell, preferably an OmniCyte.

In a further aspect, there is provided an apoptosis-modulating factor, preferably in isolated form, wherein said factor is excreted by a stem cell, preferably an OmniCyte. The apoptosis-modulating factor is obtainable from the conditioned extracellular medium of a stem cell, preferably an OmniCyte.

Also provided is a pharmaceutical composition comprising the apoptosis-modulating conditioned extracellular medium of a stem cell, preferably an OmniCyte, or an apoptosis-modulating factor secreted by a stem cell, preferably an OmniCyte, together with a pharmaceutically acceptable excipient.

Also provided is a method of producing a cell-free apoptosis-modulating conditioned extracellular medium, comprising culturing a stem cell in a medium for a suitable length of time and then collecting the extracellular conditioned medium. The extracellular conditioned medium may be separated from the stem cells using methods well known in the art such as filtration using a filter having a pore size which excludes cells, but lets macromolecules such as proteins pass through the filter.

Without wishing to be bound by theory, it seems that a stem cell, particularly an OmniCyte, secretes an apoptosis-modulating factor which can potentiate the effect of pro-apoptotic agents on hyperproliferating cells such as cancer cells. This effect seems to be particularly marked when an exogenous pro-apoptotic agent is used. The apoptosis-modulating factor is therefore preferably used to treat patients suffering from a hyperproliferative disorder who also receive treatment with a pro-apoptotic drug. The pro-apoptotic drug and the apoptosis-modulating factor may be administered simultaneously or sequentially.

The pro-apoptotic drug and the apoptosis-modulating factor may or may not form a single medicament. Preferably, they form separate medicaments and so the invention also provides an apoptosis-modulating factor secreted by a stem cell, preferably by an OmniCyte, for the treatment of a hyperproliferative disorder, wherein said factor is co-administered with the pro-apoptotic agent.

Alternatively viewed, there is provided the use of an apoptosis-modulating factor as defined herein in the manufacture of a medicament for the treatment of a hyperproliferative disorder wherein said medicament is co-administered with a pro-apoptotic agent. Preferably, said medicament potentiates the effect of the pro-apoptotic agent.

"Co-administration" may be simultaneous or sequential and by the same or different routes of administration, e.g. oral and parenteral.

In a preferred embodiment, the apoptosis-modulating factor is administered after the pro-apoptotic agent is administered. However, embodiments where the apoptosis-modulating factor is administered before or substantially simultaneously with the pro-apoptotic agent are also contemplated.

Administration of the apoptosis-modulating factor and the pro-apoptotic agent will typically be no more than 14 days apart, preferably no more than 13, 12, 11, 10, 9, 8, 7, 6, 5, 4, 3, or 2 days. More preferably, the composition/factor and the pro-apoptotic agent are administered within at most 48 hours of one another, e.g. at most 40, 35, 30, 25, 24, 23, 22, 21, 20, 19, 18, 17, 16, 15, 14, 13, 12, 11, 10, 9, 8, 7, 6, 5, 4, 3, 2 or 1 hours.

Typical treatment regimens may involve multiple administrations over the course of several days of each of the two components.

There is further provided a product containing an apoptosis-modulating factor as defined herein and a pro-apoptotic agent as a combined preparation for separate, simultaneous or sequential use in treating a hyperproliferative disorder such as cancer.

In another aspect, there is provided a method of treating a hyperproliferative disorder such as cancer, comprising administering to a subject in need thereof a therapeutically effective amount of an apoptosis-modulating factor secreted by a stem cell, preferably an OmniCyte. Preferably, said apoptosis-modulating factor is administered to a subject who also receives treatment with a pro-apoptotic drug.

In another aspect, there is provided a method of potentiating the effect of a pro-apoptotic agent on a hyperproliferative cell, preferably cancer cell, comprising the administration to a subject of an effective amount of an apoptosis-modulating factor.

Also provided are in vitro methods of modulating apoptosis, comprising the in vitro administration of an apoptosis-modulating factor as defined herein to a cell or a tissue sample. Preferably, a pro-apoptotic agent is co-administered.

The inventor has also surprisingly found that when non-cancerous cells were exposed to a pro-apoptotic agent and OmniCytes in a Transwell assay, the factor secreted by the OmniCytes had a protective effect, reducing the number of cells which underwent apoptosis compared to cells which had only been exposed to a pro-apoptotic agent. Thus, in another embodiment the apoptosis-modulating factor as defined herein may be used to reduce the amount of apoptosis of non-hyperproliferative cells, e.g. non-cancerous cells, caused by a pro-apoptotic agent. This may reduce the undesirous side-effects of chemotherapy or reduce the effects of a harmful agent to which a subject has been exposed such as alcohol.

The apoptosis-modulating factor of the invention may therefore be used to alleviate the side-effects of pro-apoptotic (cancer) drugs to improve the life quality of the patient. Alternatively, it may allow a higher dose of the pro-apoptotic cancer drug to be tolerated by the patient, allowing a more effective (cancer) treatment.

This protective effect on non-cancerous cells makes the factor of the invention particularly useful in the treatment of cancer, because it seems that it potentiates the pro-apoptotic effect of cancer drugs on cancer cells, whilst reducing the pro-apoptotic effect of cancer drugs on non-cancerous cells.

Thus, the apoptosis-modulating factor secreted by a stem cell, preferably an OmniCyte, is capable of potentiating the effect of a pro-apoptotic agent on hyperproliferative cells and it also has a protective effect on non-hyperproliferative cells, diminishing the pro-apoptotic effect of a pro-apoptotic agent on such healthy cells.

The apoptosis-potentiating effect may reside in a single agent or in a mixture of agents. The apoptosis-protective effect may also reside in a single agent or in a mixture of agents, which may be the same as, or different from, the potentiating agent(s). Thus, reference herein to a "factor" may mean a single agent or a combination of agents.

An agent is "apoptosis-potentiating" if it is capable of potentiating the effect of a pro-apoptotic agent on hyperproliferative cells. Preferably, an apoptosis-potentiating agent is capable of potentiating the effect of staurosporine, cisplatin and/or paclitaxel on cancer cells, preferably the lung cancer cell line A549. By "potentiating" is meant that the effect of the pro-apoptotic agent is increased in the presence of the potentiating agent compared to the absence of the potentiating agent. The increase in apoptosis in the presence of the apoptosis-potentiating agent is preferably at least 5%, more preferably at least 10, 15, 20, 25, 30, 35, 40, 45 or 50%, most preferably at least 60, 70 or 80%. In an preferred embodiment, the apoptosis-potentiating factor is capable of potentiating the effect of an exogenous pro-apoptotic agent, but not the effect of an endogenous pro-apoptotic agent.

An agent is "apoptosis-protecting" if it is capable of reducing the effect of a pro-apoptotic agent on non-hyperproliferative cells. Preferably, an apoptosis-protecting agent is capable of reducing the effect of staurosporine, cisplatin and/or paclitaxel on non-cancer cells, preferably healthy fibroblast cells or healthy lymphocytes. By "protecting" is meant that the effect of the pro-apoptotic agent is decreased in the presence of the potentiating agent compared to the absence of the potentiating agent. The decrease in apoptosis in the presence of the apoptosis-protecting agent is preferably at least 5%, more preferably at least 10, 15, 20, 25, 30, 35, 40, 45 or 50%, most preferably at least 60, 70 or 80%. In an preferred embodiment, the apoptosis-protecting factor is capable of diminishing the effect of an exogenous pro-apoptotic agent, but not the effect of an endogenous pro-apoptotic agent.

"Apoptosis-potentiating" and "apoptosis-protecting" are both encompassed by the term "apoptosis-modulating", so a reference to an "apoptosis-modulating" factor may be a reference to a factor which has an apoptosis-potentiating effect, or an apoptosis-protecting effect, or both.

The modulation of apoptosis may conveniently be assayed using Fluorescence activated cell sorting or immunohistochemistry as exemplified in the Examples. Briefly, cells are exposed to a pro-apoptotic agent alone (control) or to a pro-apoptotic agent and the test agent (assay) for a suitable length of time. Apoptosis may then be analysed and the percentage of apoptotic cells in the control is compared to the percentage of apoptotic cells in the assay.

Apoptosis may be analysed using the method of Ikewaki et al. 2007, where cells are stained with Annexin-V and 7-amino actinomycin (7-AAD) and then sorted by FACS.

Live, non-apoptotic cells are defined as being Annexin-V negative and 7-AAD negative, early apoptotic cells are defined as being Annexin-V positive and 7-AAD negative and late apoptotic or dead cells are defined as being Annexin-V positive and 7-AAD positive.

Alternatively, apoptosis may be analysed using immunohistochemistry. Briefly, cells are stained with 4',6-diamidino-2-phenylindole (DAPI) and visualised on a fluorescent microscope and can be analysed using the Metamorph programme. Assessment of apoptosis based on nuclear morphology using DAPI has been described by Yu et al. (1999). Cells in which the nucleus contains clearly condensed chromatin or cells exhibiting fragmented nuclei are scored as apoptotic.

The apoptosis-protective effect can also be exploited to protect non-cancerous cells from the effects of other apoptosis-inducing agents such as alcohol or thioacetamide. For example, the apoptosis-modulating factor may be used to protect liver cells from the effects of alcohol. Thus, there is provided an apoptosis-modulating factor for use in the prevention and/or amelioration of toxin-induced cellular damage, preferably alcohol-induced damage and preferably liver damage, wherein said factor is secreted by a stem cell, preferably by an OmniCyte. In a preferred embodiment, there is provided an apoptosis-modulating factor for use in reducing the effect of a pro-apoptotic agent such as alcohol on non-cancerous cells, in particular liver cells, wherein said factor is secreted by a stem cell, preferably by an OmniCyte. Also provided are methods of treating, alleviating or preventing cellular damage such as liver damage caused by a pro-apoptotic agent such as alcohol, wherein an effective amount of an apopotosis-modulating factor as defined herein is administered to a subject in need thereof.

In embodiments where the apoptosis-modulating factor is used to protect non-cancerous cells from the effects of apoptosis-inducing agents such as alcohol, the apoptosis-modulating factor may be administered prior to, simultaneously with or subsequent to the exposure of the subject to the apoptosis-inducing agent, e.g. the intake of alcohol.

OmniCytes are stem cells which are $CD34^+$, capable of self regeneration and capable of differentiation into ectodermal, mesodermal and endodermal cells, preferably into haemopoietic cells. They are further characterised by their ability to adhere to plastic (e.g. the plastic of standard tissue culture vessels) during culturing. Suitable vessels are those manufactured by Corning Incorporated, New York, USA.

OmniCytes may be further characterised by the fact that they do not require feeder layers, i.e. cells (typically inactivated by gamma irradiation which supply important metabolites without further growth or division of their own) which support the growth of the stem cells. OmniCytes can be further characterised as obtainable by:
(i) subjecting haemopoietic tissue (i.e. blood or a bone marrow sample) to density gradient separation;
(ii) exposing low density cells to an affinity ligand for CD34 (preferably attached to paramagnetic beads);
(iii) recovering cells attached to said CD34 ligand;
(iv) exposing the $CD34^+$ subpopulation to tissue culture grade plastic; and
(v) recovering $CD34^+$ cells adherent to the plastic.

A sample of OmniCytes was deposited with ECACC at Porton Down, Salisbury, SP4 0JG on 24 Sep. 2004 under accession number 04092401. The deposit was made by Professor Myrtle Gordon and the cell line was given the name "Stem Cell OmniCyte".

It is likely that other types of stem cells can also excrete the factor of the invention and so suitable types of stem cells from which the factor or equivalent factors may be isolated/which may be used to prepare a conditioned extracellular medium may include haematopoietic stem cells and mesenchymal stem cells or cells derived from OmniCytes, for example cells derived from OmniCytes after several days e.g. 7 days of culture.

"Apoptosis" is a form of programmed cell death, which can be triggered by events inside the cell such as incorrect DNA replication, or by an exogenous apoptosis-inducing agent such as staurosporine, or alcohol. Apoptosis may be contrasted with necrosis, which is cell death that does not involve programmed cell death. Necrosis may be caused by a range of different factors such as lytic agents. Apoptotic cells can be identified by using specific stains such as Annexin-V.

By a pro-apoptotic agent is meant an agent which can induce apoptosis, i.e. which can trigger the cellular pathways that lead to programmed cell death. Such agents can be contrasted with necrosis-inducing agents. Pro-apoptotic agents are well known in the art. By way of example, staurosporine, cisplatin, paclitaxel, actinomycin D, BCNU (carmustine), carboplatin, CCNU, campothecin (CPT), cantharidin, cyclophosphamide, cytarabine, dacarbazine, daunorubicin, docetaxel, doxorubicin, DTIC, epirubicin, etoposide, gefinitib, gemcitabine, ifosamide irinotecan, ionomycin, melphalan, methotrexate, mitomycin C (MMC), mitozantronemercaptopurine, oxaliplatin, PARP-1 inhibitor, taxotere, temozolomide (TZM), teniposide, topotecane, treosulfane vinorelbine, vincristine, vinblastine, 5-Azacytidine, 5,6-Dihydro-5-azacytidine and 5-fluorouracil are named herein, but this list is not intended to be limiting and the skilled person will be aware of other suitable pro-apoptotic agents. The pro-apoptotic agent is preferably an exogenous agent.

By "exogenous" agent is meant an agent which does not naturally occur in the cell, whereas an "endogenous" agent is an agent which a cell may naturally encounter. Thus, an "exogenous pro-apoptotic agent" may be contrasted with an "endogenous pro-apoptotic agent". Endogenous pro-apoptotic agents include TRAIL and TNF.

The hyperproliferative disorder may be any hyperproliferative disorder, for example selected from neoplastic disorders such as cancer, psoriatic arthritis, rheumatoid arthritis, gastric hyperproliferative disorders such as inflammatory bowel disease, skin disorders including psoriasis, Reiter's syndrome, pityriasis rubra pilaris, and hyperproliferative variants of the disorders of keratinization.

Cancer represents a hyperproliferative disorder of particular interest, and all types of cancers, including e.g. solid tumours and haematological cancers are included. Representative types of cancer include cervical cancer, uterine cancer, ovarian cancer, kidney cancer, gallbladder cancer, liver cancer, head and neck cancer, squamous cell carcinoma, gastrointestinal cancer, breast cancer, prostate cancer, testicular cancer, lung cancer, non-small cell lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer (e.g. astrocytoma, glioblastoma, medulloblastoma), neuroblastoma, sarcomas, colon cancer, rectum cancer, stomach cancer, anal cancer, bladder cancer, endometrial cancer, plasmacytoma, lymphomas, retinoblastoma, Wilm's tumor, Ewing sarcoma, melanoma and other skin cancers. Lung cancer is preferred.

In a preferred embodiment, solid tumours are treated. In another preferred embodiment, metastasis is prevented.

The subject is an animal, preferably a mammal, most preferably a human, although in one embodiment it is a non-human animal.

Attempts have been made to identify the apoptosis-modulating factor. As described in the Examples, the OmniCytes were found to excrete TNFalpha, IL-8 and Serpin E1, so these factors are potential candidates for having apoptosis-modulating activity.

The apoptosis-modulating effects of the OmniCytes were blocked when TNF activity was blocked using an antibody, indicating that the apoptosis-modulating factor may be or include a TNF-like factor such as TNF alpha.

The invention will now be described further in the following non-limiting Examples and Figures in which.

Results obtained using FACS.

Results obtained using FACS.

Results obtained using FACS.

EXAMPLES

Materials and Methods

Cell Source

The haematopoietic blood samples were obtained with informed patient consent and approval given by the local research committee. Samples of granulocyte-colony stimulating factor (G-SCF) mobilised peripheral blood progenitor cells were obtained by leukapheresis. The samples were in excess of clinical requirements and were processed by the Stem Cell Laboratory at the Hammersmith Hospital.

Isolation of CD34+ Cells

Human mobilised peripheral blood samples were diluted in a ratio of 1:4 in Hanks' buffered saline solution (HBSS) (Gibco, Paisley, UK), the mononuclear cells (MNCs) were separated by centrifugation over a Lymphoprep (Axis-Shield, UK) density gradient at 1800 rpm for 30 minutes (Hearus, UK). The MNC fraction at the interface was aspirated and washed twice with HBSS, and finally with MACS buffer (phosphate buffered saline solution (DPBS) (Gibco, UK) at pH 7.2 supplemented with 0.5% bovine serum albumin (BSA) and 2 mM EDTA). MNCs were then labelled for CD34+ isolation using CD34+ isolation kit (Miltenyi Biotec, Germany) as detailed in the manufacturer's protocol using a commercially available human CD34+MicroBead Kit together with MACS columns and separators (Miltenyi Biotec, Germany). $10^8$ mononuclear cells were incubated in 350 µl MACS buffer, 100 µl FcR blocking agent, 50 µl CD34+ magnetic beads at 4° C. for 15 minutes. Labelled cells were then washed in MACS buffer and centrifuged at 1800 rpm for 3 minutes, before being resuspended in 500 µl MACS buffer. Magnetic cell separation was performed using either Clini-MACS or MiniMACS separation column and a MACS magnetic cell separator. The column was placed in the magnetic field of a suitable MACS separator and washed with 3 ml MACS buffer. The cell suspension was then placed into the column. Unlabelled cells which passed through were collected and the column washed three times with 3 ml of MACS buffer. The column was removed from the magnetic field and 5 ml of MACS buffer was used to flush out the fraction of magnetically labelled CD34+ cells.

OmniCyte Isolation and Cell Culture

CD34+ cells were added to 25 $cm^2$ tissue-culture treated flasks (BD Biosciences, UK) at a density of $5 \times 10^6$ in HBSS (Gibco, UK) or α-MEM supplemented with 15% FBS. After 30 minutes to 2 hours, non-adherent cells were removed from the flasks by washing 3 times with HBSS (Gibco, UK). Adherent cells (OmniCytes) were consequently grown in α-Minimum Essential Medium (α-MEM) (Gibco, UK) supplemented with 30% foetal bovine serum (FBS) (Biosera, UK) and 10% GM-MIX cytokines (SCF 20 ng/mL, GM-SCF 1 ng/mL, IL-3 5 ng/mL, GSCF 100 ng/mL). Cells were incubated at 37° C. in 5% $CO_2$/95% air.

Cancer Cell Lines

Human non-small-cell lung cancer line A549 was obtained from American Type Culture Collection (catalogue number CCL-185, Rockville, Md., USA) and grown in Ham's F 12-K medium supplemented with 10% fetal bovine serum and 1% penicillin/streptomycin in a 37° C. humidified incubator with 5% $CO_2$.

Human primary fibroblasts were a obtained from the Department of Experimental Haematology, Imperial College London) and cultured in DEMM supplemented with 10% fetal bovine serum and 1% penicillin/streptomycin (Invitrogen UK) in a 37° C. air humidified incubator with 5% $CO_2$.

Apoptosis Studies

3×10$^5$ cancer cells were plated into the bottom of 24 mm Transwell 6 well plates with or without 0.4 nm pore polycarbonate membrane insert (Corning Life Sciences, USA) with 2 mL of the appropriate cell culture medium. Transwell plates with a polycarbonate membrane insert allow the exchange of soluble factors but prevent cell-cell contact, whereas Transwell plates without the membrane allow cell to cell contact. After 24 hours apoptosis was induced in cancer cells according to the designated protocol. Cells were incubated at 37° C. in 5% CO$_2$/95% air. Apoptosis was induced in cancer cells as follows; 2 μM/ml of staurosporine for 6 hours; 10 □g/ml of cis-platin for 24 hours; 2.5 μM/ml of paclitaxel for 24 hours. In fibroblasts, apoptosis was induced with 1 μM/ml staurosporine for 2 hours.

After the appropriate induction agent and duration, the culture medium was removed and the cells were washed 3 times using HBSS (Gibco, UK). 2 mL of the appropriate culture medium was then added to each of the culture wells.

To determine effect of OmniCytes on apoptosis, 3×10$^5$ OmniCytes were added 24 hours after the onset of apoptosis induction either to the top of the Transwell insert with 1 ml α-MEM (Gibco, UK) supplemented with 30% FBS (Gibco, UK) and 10% GM-MIX (for no contact conditions) or directly into the same well as the cells (for contact conditions). For the negative controls medium only (α-MEM, 30% FBS, 10% GM-MIX) was added to the inserts. Cells were incubated for 24 or 48 hours at 37° C. in 5% CO$_2$/95% air. After 24 or 48 hours the inserts were removed and the cancer cells analysed for apoptosis and Bcl-2, Bcl-xL and Bax expression.

Analysis of Apoptosis

Fluorescence Activated Cell Sorting (FACS)

Apoptosis was analysed using the method of staining with fluorescein isothiocyanate (FITC)-Annexin V and 7-AAD-FITC previously described by Ikewaki et al. (2007). Live, non-apoptotic cells were defined as being Annexin-V negative and 7-AAD negative, early apoptotic cells were defined as being Annexin-V positive and 7-AAD negative, late apoptotic cells were defined as being Annexin-V positive and 7-AAD positive. FITC-Annexin V staining was measured in FL1-H and FITC-7-AAD staining in FL3-H.

For determination of apoptosis by FACS at least 10$^5$ cells were added to FACS tubes (BD Biosciences, UK). Cells were stained according to the following manufacturer's protocol. Cells were washed twice with cold PBS and then re-suspended in 100 μl of Annexin-V Binding Buffer (BD Biosciences, UK). 2 μl of FITC-Annexin V and 2 μl of FITC-7-AAD were added to each tube and incubated at room temperature in the dark for 15 minutes. After 15 minutes 300 μl of Annexin V binding buffer was added to stop the reaction. Cells were then analysed using a FACSCalibur Flow Cytometer (BD Biosciences, UK) and CellQuest Pro software (BD Biosciences, UK) at least 10$^5$ cells were analysed. All the experiments were performed in triplicates and repeated at least 3 times.

Immunocytochemistry

10$^5$ cells were fixed using 4% paraformaldehyde (PFA) for 15 minutes at room temperature and washed 3 times with PBS (Gibco, UK). Cells were stained with 4',6-diamidino-2-phenylindole (DAPI) (Vector Laboratories, Burlingame, US). Cells were visualised on a Zeiss fluorescent microscope and analysed using the Metamorph programme.

Assessment of apoptosis was based on nuclear morphology using DAPI that has been described previously Yu et al. (1999). Briefly, cells in which the nucleus contained clearly condensed chromatin or cells exhibiting fragmented nuclei were scored as apoptotic.

$$\text{Apoptosis (\%)} = \frac{\text{Number of Apoptotic Cells}}{\text{Total Number Cells Counted}} \times 100$$

For each sample, a minimum of 5 random fields were assessed and at least 250 cells were counted. All the experiments were performed in triplicates and repeated at least 3 times.

RESULTS

1. Effect on Cancer Cells

The A549 lung cancer cell line was exposed to the apoptosis-inducing agent staurosporine.

Figure 1:
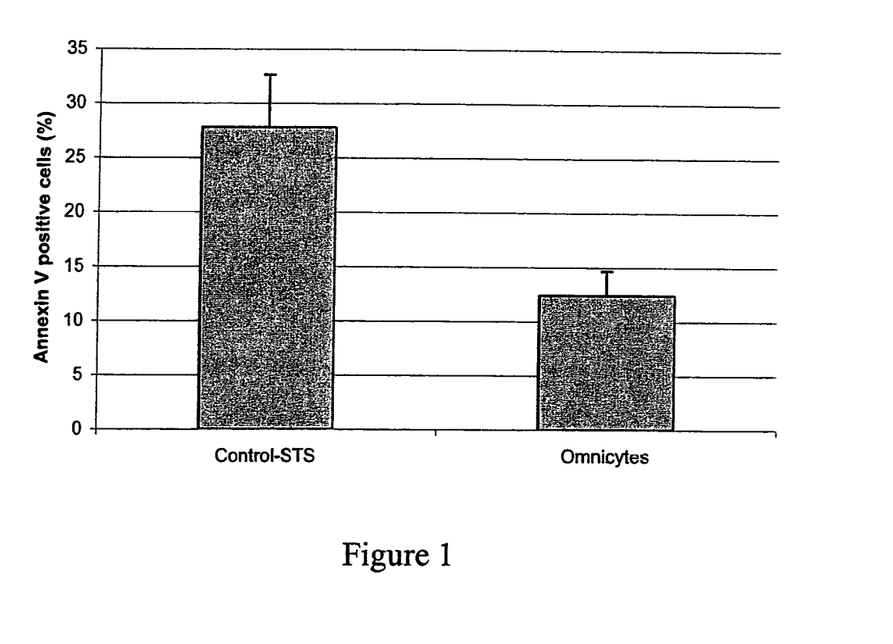
FIG. 1 is a graph showing the effect of OmniCytes onto lung cancer cells treated with staurosporine in an assay which allows direct cell contact. Annexin V is a measure of the percentage of apoptotic cells. Annexin V positive cells (%) are shown on the Y-axis. Control: treatment with staurosporine alone. Assay: Treatment with staurosporine and OmniCytes (direct cell contact). Results obtained using FACS.

Under co-culture conditions, i.e. with cell contact, a significant decrease in cancer cell apoptosis was observed in the cells contacted with OmniCytes compared to the control cells. FACS analysis showed that the mean of apoptosis of the OmniCyte group was significantly lower than the control group: 12.43%±2.24 and 22.77%±4.87 respectively (p=0.028, Wilcoxon test) (FIG. 1).

Figure 2:
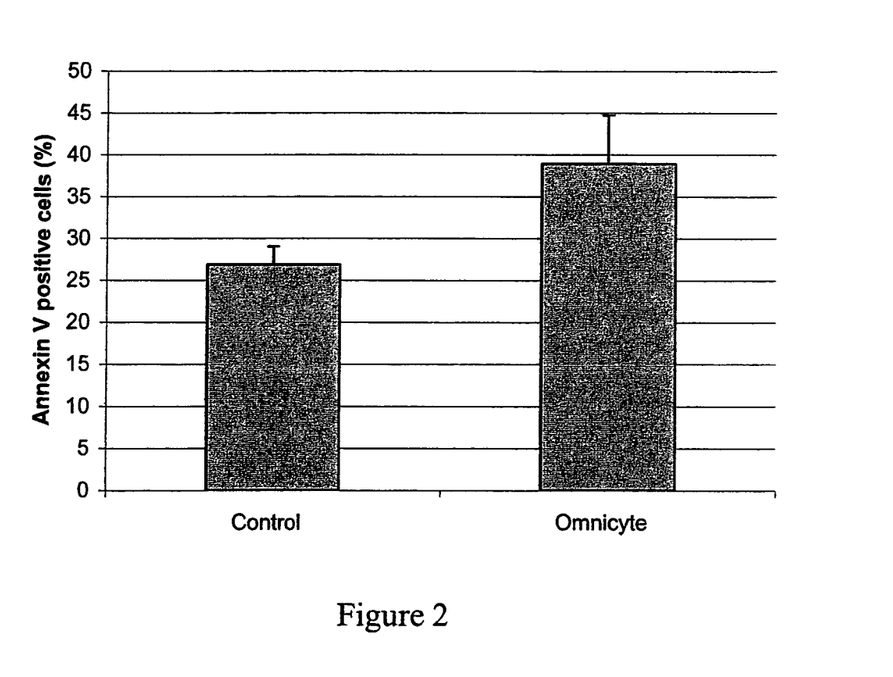
FIG. 2 is a graph showing the effect of OmniCytes onto lung cancer cells treated with staurosporine in an assay which does not allow direct cell contact (Transwell assay). Annexin V is a measure of the percentage of apoptotic cells. Annexin V positive cells (%) are shown on the Y-axis. Control: treatment with staurosporine alone. Assay: Treatment with staurosporine and OmniCytes (no cell contact).
Figure 3:
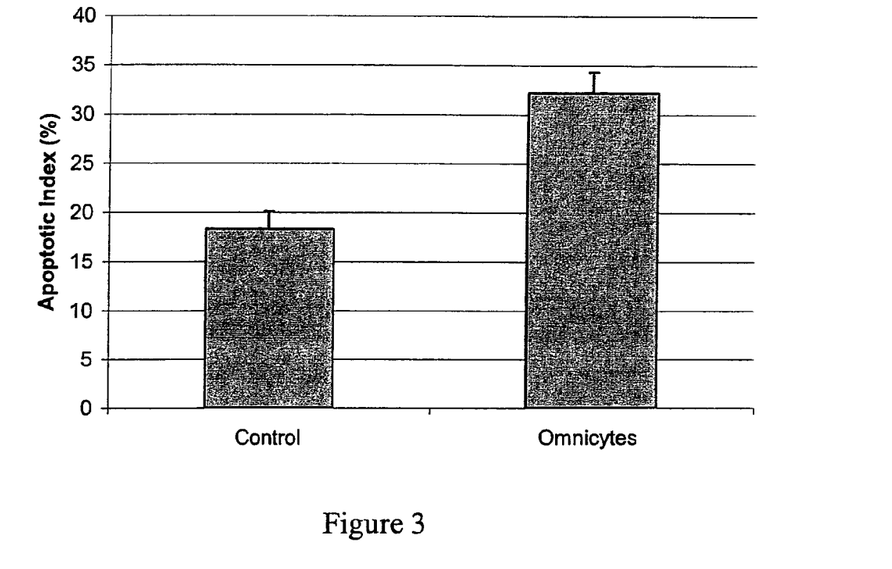
FIG. 3 shows the results of the assay of FIG. 2, as measured using immunofluorescense.

Under conditions which did not allow cell contact (Transwell plate with membrane) we have observed a significant increase of apoptosis by FACS analysis in six different experiments (FIG. 2): 38.88%±5.86 in the OmniCyte group versus 26.85%±2.15 in control group (p=0.028, Wilcoxon test). These results are confirmed by nuclear staining (DAPI) with immuno-fluorescent microscopy (FIG. 3): 32.20%±2.1 in the OmniCyte group versus 18.32%±1.81 in the control group (p=0.043, Wilcoxon test).

The effect of OmniCytes on cells which had not been exposed to an apoptosis-inducing agent was also tested using FACS and immuno-fluorescent analysis. No significant variation of apoptosis levels with or without cell contact was observed (data not shown).

Figure 4:
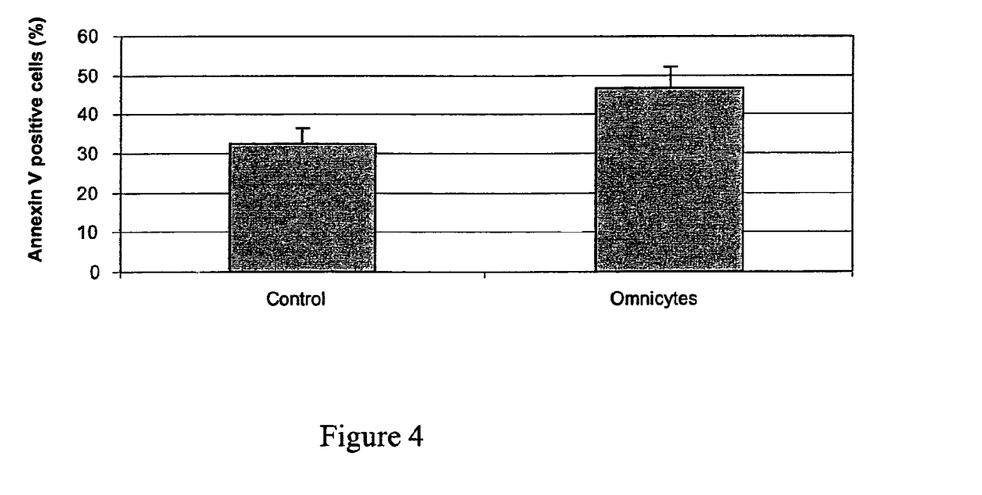
FIG. 4 is a graph showing the effect of OmniCytes onto lung cancer cells treated with paclitaxel in an assay which does not allow direct cell contact (Transwell assay). Annexin V is a measure of the percentage of apoptotic cells. Annexin V positive cells (%) are shown on the Y-axis. Control: treatment with paclitaxel alone. Assay: Treatment with paclitaxel and OmniCytes (no cell contact).

These effects of OmniCytes are reproducible with other chemotherapeutic agents. The same pattern, i.e. a decrease in cancer cell apoptosis under co-culture conditions and an increase in cancer cell apoptosis under conditions which do not allow cell contact, but which allow diffusion of factors, was observed with other apoptosis-inducing agents such as cis-platin and paclitaxel. For example, when paclitaxel was used with OmniCytes under no cell contact conditions, a significant rise of the apoptosis level in the OmniCytes group was observed compared to the control group (FIG. 4) (p=0.043, Wilcoxon test).

2. Effect on Non-Cancer Cells

Figure 5:
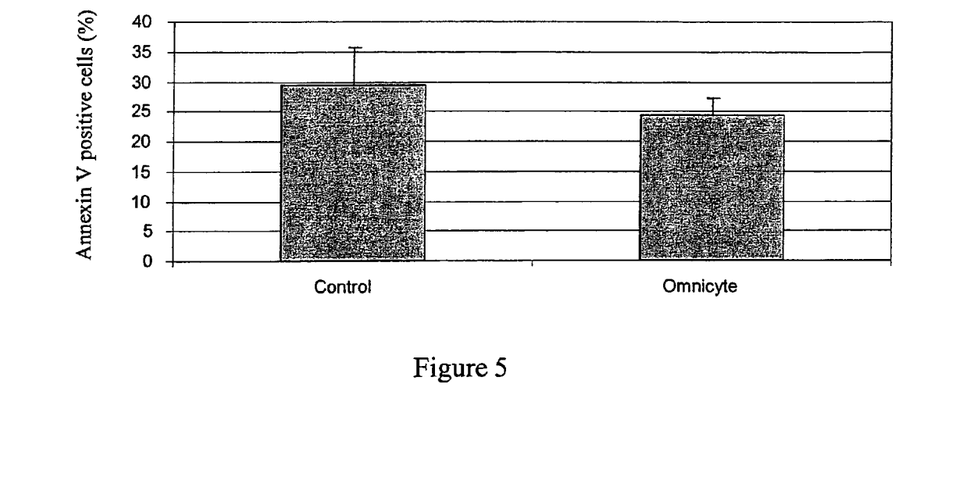
FIG. 5 is a graph showing the effect of OmniCytes onto fibroblast cells treated with staurosporine in an assay which does not allow direct cell contact (Transwell assay). Annexin V is a measure of the percentage of apoptotic cells. Annexin V positive cells (%) are shown on the Y-axis. Control: treatment with staurosporine alone. Assay: Treatment with staurosporine and OmniCytes (no cell contact).

Under conditions which did not allow cell contact (Transwell plate with membrane), OmniCytes appeared to protect human fibroblasts from the pro-apoptotic effects of staurosporine (FIG. 5).

3. Cytokine Production

Using a semi-quantitative kit to analyse cytokine levels in the extracellular medium of cells, three cytokines which are secreted at higher levels in the OmniCytes gimp versus control were identified. These cytokines are: TNF alpha, IL-8 and Serpin E1.

4. Caspase Activation

Figure 6:
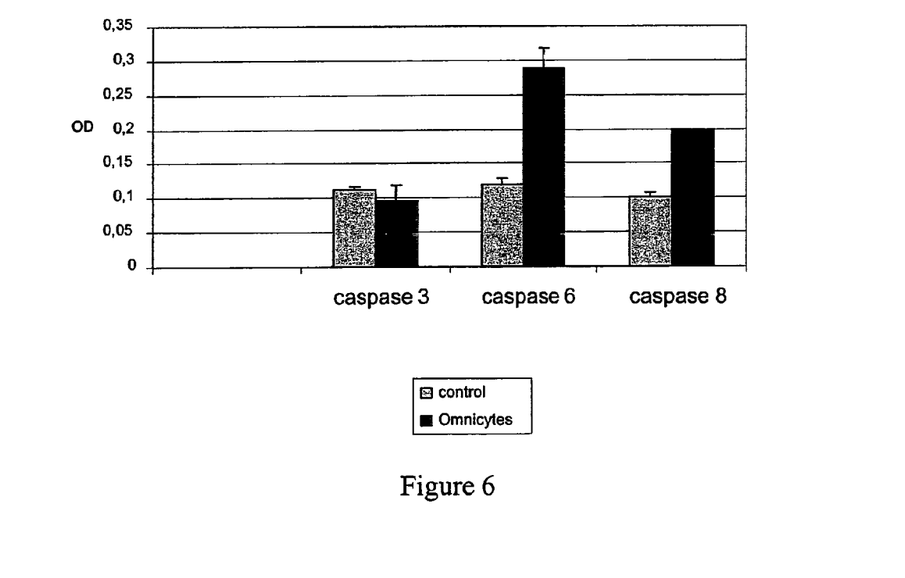
FIG. 6 is a graph showing the level of activity of caspase 3, caspase 6 or caspase 8 in OmniCyte and control group.

Under no cell-contact conditions, an increase in Caspase 6 and 8 activity, but not caspase 3 activity, was observed in the OmniCyte compared to the control group (FIG. 6).

5. Antibody Studies

Figure 7:
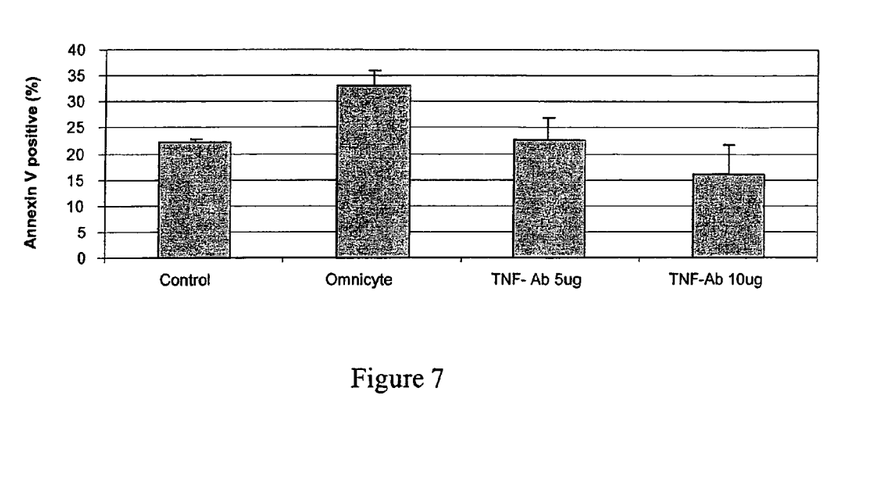
FIG. 7 is a graph showing the effect of TNF-alpha-blocking antibodies at 5 □g or 10 □g onto lung cancer cells treated with staurosporine and OmniCytes (no direct cell contact). The apoptosis-increasing effects of the OmniCytes compared to the control are shown, but this effect is abolished by the TNF-alpha-blocking antibodies.

The effect of TNF-alpha blocking antibodies was tested. A549 lung cancer cells were exposed to staurosporine and OmniCytes were added without direct cell contact. The control was OmniCyte-free. TNF-alpha blocking antibodies (Abcam™, Cambridge, UK) at two different concentrations (5 or 10 µg/mL) were added. There was a significant increase in apoptosis in the OmniCyte group versus the control (32.89%±2.94 versus 22.13%±0.74) and a significant decrease in the group of 5 µg (22.56%±4.44) and even more marked in the group of 10 µg (16.14%±5.52) TNF blocking antibodies compared to the OmniCytes group (32.89%±2.94) (FIG. 7). This indicates that OmniCytes induce an extrinsic apoptotic pathway via TNF receptor activation.

6. Inhibition of Liver Cell Death by OmniCytes

Figure 8:
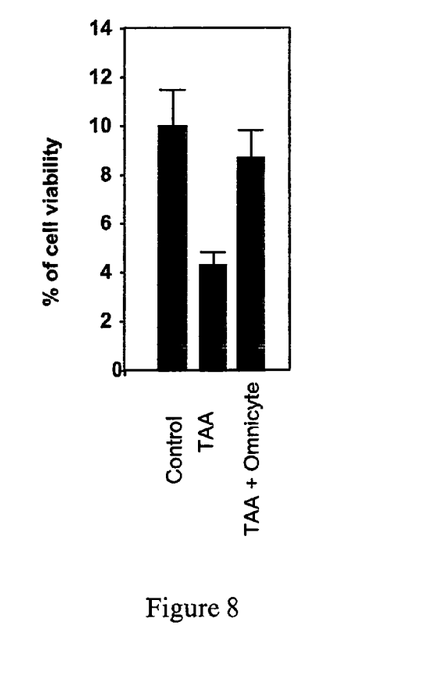
FIG. 8 is a graph showing the effect of thioacetamide (TAA) onto the viability of liver cells. Viability is significantly reduced. This effect is significantly inhibited by OmniCytes when used without direct cell contact.

Rat liver cells were exposed to the hepatotoxin thioacetamide (TAA), which induces liver damage such as cirrhosis and fibrosis. The control was only exposed to TAA, whereas the experimental group was also exposed to OmniCytes without cell contact. Cell viability (expressed as mitochondrial dehydrogenase activity) was assessed. Exposure to TAA significantly decreased cell viability, and this effect could be prevented, counter-acted or reversed by a factor secreted by OmniCytes (FIG. 8).

Figure 9:
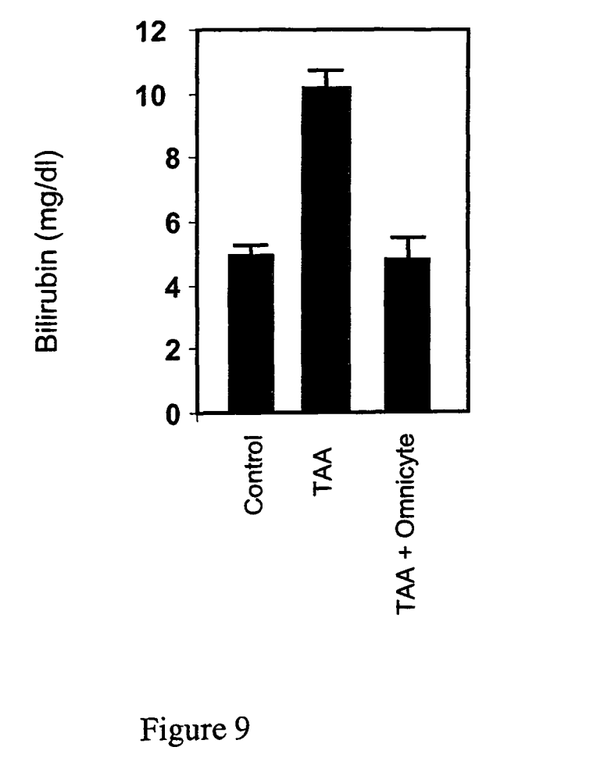
FIG. 9 is a graph showing the levels of bilirubin, which is a measure of liver cell health. TAA causes an undesirable increase in bilirubin levels and this is entirely inhibited by OmniCytes when used without direct cell contact.

Liver function was also assayed by measuring bilirubin levels. Aberrantly high levels of bilirubin are typically indicative of a liver disorder or malfunction. TAA caused bilirubin levels to rise, and this was prevented, counter-acted or reversed by a factor secreted by OmniCytes (FIG. 9).

The invention claimed is:

1. An apoptosis-modulating cell-free composition comprising serum-free conditioned extracellular medium of a stem cell, wherein said stem cell is CD34+, capable of self-regeneration and capable of differentiation into ectodermal, mesodermal and endodermal cells and is characterized by its ability to adhere to plastic during culturing, and has the identifying characteristics of a cell having accession number ECACC 0409240, deposited at Porton Down, Salisbury, SP4 0JG on Sep. 24, 2004.

2. An apoptosis-modulating cell-free composition according to claim 1, wherein said conditioned extracellular medium is obtainable by culturing said stem cell for 12-72 hours.

* * * * *